(12) United States Patent
Siemer et al.

(10) Patent No.: US 8,927,737 B2
(45) Date of Patent: Jan. 6, 2015

(54) PROCESS FOR PURIFYING IONIC LIQUIDS

(75) Inventors: Michael Siemer, Mannheim (DE);
Michael Klein, Reichenbach-Steegen (DE); Sunghee Son, Mannheim (DE);
Klemens Massonne, Bad Duerkheim (DE); Uwe Vagt, Mannheim (DE)

(73) Assignee: BASF SE, Ludwigshafen (DE)

( * ) Notice: Subject to any disclaimer, the term of this patent is extended or adjusted under 35 U.S.C. 154(b) by 159 days.

(21) Appl. No.: 13/570,539

(22) Filed: Aug. 9, 2012

(65) Prior Publication Data

US 2013/0041159 A1    Feb. 14, 2013

Related U.S. Application Data

(60) Provisional application No. 61/521,384, filed on Aug. 9, 2011.

(51) Int. Cl.
    *C07D 233/58*      (2006.01)

(52) U.S. Cl.
    CPC .................................. *C07D 233/58* (2013.01)
    USPC ....................................................... 548/335.1

(58) Field of Classification Search
    USPC ....................................................... 548/335.1
    See application file for complete search history.

(56) References Cited

U.S. PATENT DOCUMENTS

| | | | |
|---|---|---|---|
| 4,361,336 A | 11/1982 | Reeh et al. | |
| 4,454,172 A | 6/1984 | Heinrich et al. | |
| 5,580,659 A | 12/1996 | Toerner et al. | |
| 2002/0066491 A1 | 6/2002 | Lively | |
| 2003/0220449 A1 | 11/2003 | Jacques et al. | |
| 2004/0188350 A1 | 9/2004 | Beste et al. | |
| 2007/0235696 A1 | 10/2007 | Burrell et al. | |
| 2012/0234766 A1 | 9/2012 | Siemer et al. | |

FOREIGN PATENT DOCUMENTS

| | | |
|---|---|---|
| DE | 24 58 733 B1 | 7/1975 |
| DE | 30 06 961 A1 | 8/1980 |
| DE | 33 05 158 A1 | 8/1984 |
| DE | 42 01 113 C1 | 1/1993 |
| DE | 42 08 047 C1 | 11/1993 |
| DE | 103 37 707 A1 | 4/2005 |
| EP | 0 296 852 A2 | 12/1988 |
| EP | 0 346 101 A2 | 12/1989 |
| EP | 0 434 244 A2 | 6/1991 |
| EP | 1 329 481 A2 | 7/2003 |
| EP | 1 470 846 A1 | 10/2004 |
| EP | 1 512 710 A2 | 3/2005 |
| EP | 1 518 901 A2 | 3/2005 |
| EP | 1 690 889 A1 | 8/2006 |
| EP | 1 690 890 A1 | 8/2006 |
| JP | 01197526 A | 8/1989 |
| JP | 01236238 A | 9/1989 |
| WO | WO 96/34909 A1 | 11/1996 |
| WO | WO 98/47940 A1 | 10/1998 |
| WO | WO 00/04106 A1 | 1/2000 |
| WO | WO 00/66650 A2 | 11/2000 |
| WO | WO 01/66633 A1 | 9/2001 |
| WO | WO 02/094922 A1 | 11/2002 |
| WO | WO 03/066704 A1 | 8/2003 |
| WO | WO 03/093374 A2 | 11/2003 |
| WO | WO 2006/079890 A1 | 8/2006 |
| WO | WO 2008/140496 A2 | 11/2008 |

OTHER PUBLICATIONS

International Search Report and Written Opinion issued Sep. 6, 2012 in PCT/EP2012/065542 filed Aug. 8, 2012 (with English Translation).

*Primary Examiner* — Rebecca Anderson
(74) *Attorney, Agent, or Firm* — Oblon, Spivak, McClelland, Maier & Neustadt, L.L.P.

(57) ABSTRACT

The present process purifies a salt $Cat^+X^-$, where $Cat^+$ is any cation and $X^-$ is an organic anion having at least 6 carbon atoms. The salt is an impurity in a composition comprising a water-soluble salt $(Cat^+)_n Y^{n-}$, where $Y^{n-}$ is an inorganic anion or an organic anion, different from $X^-$, with at most 10 carbon atoms. The process involves converting $X^-$ into an acid HX by adding an acid $(H^+)_m Z^{m-}$, forming two phases: an organic phase comprising HX and an aqueous phase comprising the water-soluble salts $(Cat^+)_m Z^{m-}$ and $(Cat^+)_n Y^{n-}$ or acids $(H^+)_n Y^{n-}$. The organic phase is separated and the aqueous phase passes over a basic anion exchanger which binds $Z^{m-}$ and $Y^{n-}$ and liberates $OH^-$, giving an aqueous mixture comprising $Cat^+OH^-$. The organic phase and the aqueous mixture are converted into $Cat^+X^-$ and $H_2O$, optionally with addition of further HX.

19 Claims, No Drawings

PROCESS FOR PURIFYING IONIC LIQUIDS

The invention relates to a process for purifying salts $Cat^+X^-$, where $Cat^+$ is any cation and $X^-$ is an organic anion having at least 6 carbon atoms, wherein
   a) the salts $Cat^+X^-$ are present in compositions comprising water-soluble salts $(Cat^+)_n Y^{n-}$, where $Cat^+$ is the above cation, $Y^{n-}$ is an inorganic anion or an organic anion which is different from $X^-$ and has not more than 10 carbon atoms and n is 1, 2 or 3 as impurities,
   b) the anions $X^-$ of the salts $Cat^+X^-$ are converted by addition of a water-soluble protic acid $(H^+)_m Z^{m-}$, where m is 1, 2 or 3, into the acids HX, forming two phases, namely an organic phase comprising HX and an aqueous phase comprising the water-soluble salts $(Cat^+)_m Z^{m-}$ and $(Cat^+)_n Y^{n-}$ or acids $(H^+)_n Y^{n-}$,
   c) the organic phase is separated off,
   d) the aqueous phase is passed over a strongly basic anion exchanger which binds the anions $Z^{m-}$ and $Y^{n-}$ and liberates $OH^-$ so as to give an aqueous mixture comprising $Cat^+ OH^-$ and
   e) the organic phase (comprising HX) and the aqueous mixture obtained (comprising CatH) are, optionally with addition of further HX, converted into $Cat^+X^-$ and $H_2O$.

Salts having an organic cation are, for example, important as ionic liquids. Ionic liquids have a melting point of less than 200° C., in particular less than 100° C.

There are a large number of industrial uses for ionic liquids, e.g. as solvents. In the uses, ionic liquids are generally not consumed but merely contaminated. Since they are expensive salts, there is a need for a particularly effective and advantageous process for working up the mixtures obtained after use, so that reuse can occur.

The use of ionic liquids for dissolving cellulose results in formation of, for example, mixtures which comprise not only the ionic liquid but also solvent, in particular water, impurities introduced, e.g. introduced acids, salts or degradation products of cellulose and the ionic liquid. Degradation products of cellulose are, in particular, short-chain carboxylic acids which are then, due to equilibrium reactions, also present as anions associated with the cation of the ionic liquid. Inorganic cations can also be present as impurities. Chloride is particularly undesirable since it can lead to corrosion of plant components.

To reuse the ionic liquid, there is a need for a simple and effective process for separating off acids and anions thereof present in salts, in particular short-chain carboxylic acids and the anions thereof and also undesirable inorganic anions.

A process for separating off acids using a weakly basic ion exchanger is known from the earlier European patent application having the application number 11158189.8 (PF 71814), which is not a prior publication. The process is not suitable for separating off salts and anions thereof.

Weakly basic ion exchangers are ion exchangers which comprise a polymer having primary, secondary or tertiary amino groups as ion-exchange polymer and can thus bind acids. Here, the acid proton becomes attached to the amino group (quaternization) and the acid anion is bound as counteranion. Anions of salts can therefore not be separated off in this way.

A process by means of which the anions of salts, in particular short-chain anions of carboxylic acids, can also be separated off is therefore desired.

In the process having the application number 11158189.8 (PF 71814), all acids are separated off, in small amounts also the protic acid of the anion of the ionic liquid since the anions of the ionic liquid are in thermodynamic equilibrium with the associated protic acids. A process in which the acids of the anion of the ionic liquids which have been separated off in this way can be used for renewed formation of the ionic liquid is therefore desired.

It is therefore an object of the present invention to provide a simple and effective process for separating undesirable anions from ionic liquids or compositions comprising ionic liquids.

We have accordingly found the process defined at the outset.

Process Step a)

In a preferred embodiment, the salts $Cat^+X^-$ have a melting point of less than 100° C. (1 bar, atmospheric pressure); the salts $Cat^+X^-$ are therefore ionic liquids.

In particular, the salts $Cat^+X^-$ are liquid under standard conditions (21° C., 1 bar).

The cation $Cat^+$

Suitable organic cations Cat are, in particular, organic compounds having heteroatoms such as nitrogen, sulfur, oxygen or phosphorus.

In particular, the organic cations are compounds having an ammonium group (ammonium cations), an oxonium group (oxonium cations), a sulfonium group (sulfonium cations) or a phosphonium group (phosphonium cations).

Preference is given to an organic cation having at least one nitrogen atom.

In a particular embodiment, the organic cations are ammonium cations, which for the present purposes encompass
   nonaromatic compounds having a localized positive charge on the nitrogen atom, e.g. compounds having tetravalent nitrogen (quaternary ammonium compounds) or compounds having trivalent nitrogen, with one bond being a double bond, or
   aromatic compounds having a delocalized positive charge and at least one nitrogen atom, preferably from one to three nitrogen atoms, in the aromatic ring system.

Preferred organic cations are quaternary ammonium cations, preferably those having three or four aliphatic substituents, particularly preferably C1-C12-alkyl groups, on the nitrogen atom, which substituents may also be substituted by hydroxyl groups.

Preference is likewise given to organic cations which comprise a heterocyclic ring system, where at least one nitrogen atom, preferably from one to three nitrogen atoms, is/are constituent of the ring system.

Possibilities are monocyclic, bicyclic, aromatic or nonaromatic ring systems. Mention may be made by way of example of bicyclic systems as are described in WO 2008/043837. The bicyclic systems of WO 2008/043837 are diazabicyclo derivatives, preferably made up of a 7-membered ring and a 6-membered ring, which comprise an amidinium group; particular mention may be made of the 1,8-diazabicyclo[5.4.0]undec-7-enium cation.

Very particular preference is given to cations which comprise a heterocyclic ring system having one or two nitrogen atoms as constituent of the ring system.

Possible organic cations of this type are, for example, pyridinium cations, pyridazinium cations, pyrimidinium cations, pyrazinium cations, imidazolium cations, pyrazolium cations, pyrazolinium cations, imidazolinium cations, thiazolium cations, triazolium cations, pyrrolidinium cations and imidazolidinium cations. These cations are, for example, described in WO 2005/113702. If it is necessary for a positive charge on the nitrogen atom or in the aromatic ring system, the nitrogen atoms are in each case substituted by a hydrogen atom or an organic group which generally has not more than 20 carbon atoms, preferably a hydrocarbon group, in particular a C1-C16-alkyl group, in particular a C1-C10-alkyl group, particularly preferably a C1-C4-alkyl group.

The carbon atoms of the ring system can also be substituted by organic groups which generally have not more than 20 carbon atoms, preferably a hydrocarbon group, in particular a C1-C16-alkyl group, in particular a C1-C10-alkyl group, particularly preferably a C1-C4-alkyl group.

Particularly preferred ammonium cations are quaternary ammonium cations, imidazolium cations, pyrimidinium cations and pyrazolium cations.

The organic cation is particularly preferably an imidazolium cation of the formula I below,

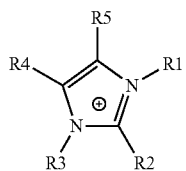

where

R1 is an organic radical having from 1 to 20 carbon atoms and

R2, R3, R4 and R5 are each an H atom or an organic radical having from 1 to 20 carbon atoms.

In formula I, preference is given to R1 and R3 each being, independently of one another, an organic radical having from 1 to 10 carbon atoms. In particular, R1 and R3 are each an aliphatic radical, in particular an aliphatic radical without further heteroatoms, e.g. an alkyl group. Particular preference is given to R1 and R3 each being, independently of one another, a C1-C10-alkyl group or a C1-C4-alkyl group.

In formula I, preference is given to R2, R4 and R5 each being, independently of one another, an H atom or an organic radical having from 1 to 10 carbon atoms; in particular, R2, R4 and R5 are each an H atom or an aliphatic radical. Particular preference is given to R2, R4 and R5 each being, independently of one another, an H atom or an alkyl group; in particular, R2, R4 and R5 are each, independently of one another, an H atom or a C1-C4-alkyl group. Very particular preference is given to R2, R4 and R5 each being an H atom.

The anion $X^-$ $X^-$ is an organic anion having at least 6, in particular at least 8, carbon atoms. In general, $X^-$ comprises not more than 30, in particular not more than 20, carbon atoms.

In particular, $X^-$ is an anion having a carboxylate, sulfonate or sulfate group.

In a preferred embodiment, $X^-$ does not comprise any further heteroatoms apart from the oxygen atoms and sulfur atoms in the carboxylate, sulfonate or sulfate group. In particular, the anion $X^-$ comprises an anionic group selected from among a carboxylate, sulfonate or sulfate group and in addition a hydrocarbon radical without further heteroatoms or functional groups.

Suitable anions having a sulfate group are, in particular, anions of the formula $R_a$—O—$SO_3^-$, where $R_a$ is a C6-C20-alkyl group.

Suitable anions having a sulfonate group are, in particular, anions of the formula $R_b$—$SO_3^-$, where $R_b$ is a C6-C20-alkyl group.

In particular, $X^-$ is an organic anion having a carboxylate group.

As carboxylates of this type, particular mention may be made of organic compounds which have from 6 to 20 carbon atoms and comprise a carboxylate group.

The carboxylates can be either aliphatic or aromatic carboxylates; for the present purposes, aromatic carboxylates are carboxylates comprising aromatic groups. Particular preference is given to aliphatic or aromatic carboxylates which do not comprise any further heteroatoms apart from the oxygen atoms of the carboxylate group, e.g. the carboxylates of alkanecarboxylic acids, alkenecarboxylic acids, alkynecarboxylic acids, alkadienecarboxylic acids, alkatrienecarboxylic acids, benzoic acid or phenylacetic acid. Suitable carboxylates of alkanecarboxylic acids, alkenecarboxylic acids and alkadienecarboxylic acid are also known as fatty acid carboxylates.

$X^-$ is particularly preferably a C6-C20-alkanoate.

Very particular preference is given to C6-C20-alkanoates (carboxylates of alkanecarboxylic acids), in particular C8-C16-alkanoates.

Particular mention may be made of the carboxylates of n-caproic acid (C6-carboxylic acid) n-caprylic acid (C8-carboxylic acid, octanoic acid), n-capric acid (C10-carboxylic acid, decanoic acid), lauric acid (C12-carboxylic acid, dodecanoic acid), palmitic acid (C16-carboxylic acid, hexadecanoic acid) or stearic acid (C18-carboxylic acid). In a particular embodiment, the anions of the salts are carboxylates of C6-C20-alkanecarboxylic acids, i.e. C6-C20-alkanoates. Particular mention may be made of C8-C16-alkanoates and in a particular embodiment C8-C12-alkanoates.

The protic acids HX of the anions $X^-$ are not soluble in water or have only a limited solubility in water. At 20° C., 1 bar, preference is given to not more than 100 gram of HX dissolved in 1000 gram of water; in particular, not more than 50 gram of HX dissolved in 1000 gram of water, very particularly preferably not more than 20 gram of HX dissolved in 1000 gram of water; in a particular embodiment, not more than 10 gram or not more than 5 gram of HX dissolved in water.

Examples of salts $Cat^+X^-$ are:
1-ethyl-3-methylimidazolium octanoate,
1-methyl-3-methylimidazolium octanoate,
1-ethyl-3-ethylimidazolium octanoate,
1-ethyl-3-methylimidazolium ethylhexanoate,
1-methyl-3-methylimidazolium ethylhexanoate,
1-ethyl-3-ethylimidazolium ethylhexanoate,
1-ethyl-3-methylimidazolium isononanoate,
1-methyl-3-methylimidazolium isononanoate,
1-ethyl-3-ethylimidazolium isononanoate.

Further constituents of the compositions used under a)

The composition used in a) comprises, in addition to the salts $Cat^+X^-$, water-soluble salts $(Cat^+)_n Y^{n-}$, where $Cat^+$ is the above cation, $Y^{n-}$ is an inorganic anion or an organic anion which is different from $X^-$ and has not more than 10 carbon atoms and n is 1, 2 or 3, as impurities. In particular n is 1 or 2, particularly preferably 1.

The water-soluble salts $(Cat^+)_n Y^{n-}$ preferably have a solubility in water of more than 50 gram, in particular more than 100 gram, particularly preferably more than 200 gram, in 1000 gram of water (20° C., 1 bar). If $(Cat^+)_n Y^{n-}$ are ionic liquids, they are, in the liquid state, preferably miscible in any ratio with water.

Possible inorganic anions are, in particular, chloride and sulfate.

As organic anions, mention may be made by way of example of those having not more than 8 carbon atoms, in particular not more than 6 carbon atoms or not more than 4 carbon atoms.

The organic anions are, in particular, organic anions having at least one carboxylate group, at least one sulfonate group or at least one sulfate group.

In particular, the anions can be anions having at least one carboxylate group (carboxylates for short).

In a preferred embodiment, carboxylates $Y^{n-}$ have one or two carboxylate groups.

As carboxylates $Y^{n-}$ having one carboxylate group, particular mention may be made of formic acid (C1-carboxylic acid), acetic acid (C2-carboxylic acid), propionic acid (C3-carboxylic acid), n-butyric acid (C4-carboxylic acid).

The carboxylates $Y^{n-}$ can be aliphatic or aromatic carboxylates; for the purposes of the present invention, aromatic carboxylates are carboxylates comprising aromatic groups. Possibilities also include, in particular, carboxylates which comprise further functional groups, e.g. hydroxyl groups, ether groups or carbonyl groups.

Mention may be made by way of example of anions of glycolic acid, furandicarboxylic acid, levulinic acid (4-oxopentanoic acid).

The composition can comprise various salts $(Cat^+)_n Y^{n-}$; in particular, it can comprise various salts having an inorganic anion $Y^{n-}$ and at the same time various salts having an organic anion $Y^{n-}$.

The total content of all salts $(Cat^+)_n Y^{n-}$ will generally be not more than 200 parts by weight, in particular not more than 100 parts by weight or not more than 50 parts by weight, of $(Cat^+)_n Y^{n-}$ per 100 parts by weight of $Cat^+X^-$; in general, the total content of all salts $(Cat^+)_n Y^{n-}$ is at least 1 part, in particular at least 5 parts, by weight per 100 parts by weight of $Cat^+X^-$.

The water-soluble salts $(Cat^+)_n Y^{n-}$ are impurities and can have got into the composition in various ways. They can have been introduced or formed by previous uses of the ionic liquid $Cat^+X^-$; they can have been formed, for example, as degradation product of compounds with which the ionic liquid has come into contact in a previous use. For example, they can be degradation products of cellulose when the ionic liquid has previously been used as solvent for cellulose.

The composition used in a) can comprise further constituents. In particular, the composition can comprise solvent or further impurities which have been introduced by the previous use of the ionic liquid. Solvents which can have been introduced in a previous use are, in particular, solvents which are miscible with the ionic liquid $Cat^+X^-$, e.g. methanol, ethanol or water. When the ionic liquid is used as solvent for cellulose, water serves as precipitate in order to precipitate cellulose in the desired form, e.g. as fiber, film or beads.

The composition used in a) therefore comprises, in particular, water.

In a preferred embodiment, the composition used in a) comprises more than 80% by weight, particularly preferably more than 90% by weight, of the salts $Cat^+X^-$ and optionally a solvent miscible therein, in particular water.

Here, the proportion of $Cat^+X^-$ can be, for example, from 10 to 95% by weight, in particular from 40 to 90% by weight or in a particular embodiment from 70 to 90% by weight, and the proportion of the solvent (water) can correspondingly be from 5 to 90% by weight, in particular from 10 to 60% by weight and in a particular embodiment from 10 to 30% by weight, where the percentages by weight are based on the total weight of $Cat^+X^-$ and the solvent (water).

Possible further impurities are, for example, those which dissolve in the ionic liquid $Cat^+X^-$ or the solvent or are miscible therewith.

Mention may be made by of example of hemicelluloses; these can have been introduced in the use of the ionic liquid as solvent for cellulose.

In a particular embodiment, the compositions used in a) therefore also comprise hemicelluloses, i.e. water-soluble low molecular weight degradation products or constituents of cellulose, e.g. hexoses, pentoses and oligomeric hexoses or pentoses. Water-soluble oligomeric hexoses or pentoses usually have a molecular weight of less than 5000 g/mol.

The content of hemicelluloses in the composition can be, for example, from 0.1 to 5 parts by weight, in particular from 0.5 to 5 parts by weight, of hemicellulose per 100 parts by weight of the total weight of salts $Cat^+X^-$ and solvent.

Process Step b)

In process step b), a water-soluble protic acid $(H^+)_m Z^{m-}$ is added to the composition. m is, in particular, 1 or 2.

The water-soluble protic acid $(H^+)_m Z^{m-}$ preferably has a solubility in water of at least 200 gram, in particular at least 400 gram, in 1000 gram of water (20° C., 1 bar); in particular, it is miscible in any ratios with water.

The pKa of the protic acid $(H^+)_m Z^{m-}$ is preferably smaller than the pKa of HX, i.e. the acid strength of $(H^+)_m Z^{m-}$ is greater.

The pKa is the negative logarithm to the base 10 of the acid constant, Ka.

The pKa is for this purpose measured at 25° C., 1 bar in water or dimethyl sulfoxide as solvent. It is therefore sufficient for the acid to have the corresponding pKa either in water or in dimethyl sulfoxide. The pKa is preferably measured in water. Dimethyl sulfoxide is used particularly when the anion is not sufficiently soluble in water. Information on both solvents may be found in standard works.

In particular, the pKa of the acid HX is at least 0.1 greater, particularly preferably at least 0.5 greater, very particularly preferably at least 1 greater and in a particular embodiment at least 2 greater, than the pKa of $(H^+)_m Z^{m-}$.

The protic acids HX preferably have a pKa of greater than 2, preferably greater than 3, particularly preferably greater than 4. For example, octanoic acid has a pKa of 4.8.

A suitable protic acid $(H^+)_m Z^{m-}$ is, for example, sulfuric acid having a pKa of −3; however, acids whose pKa is only slight less the pKa of HX are also suitable for the process of the invention; thus, for example in the case of octanoic acid as HX it is possible to use acetic acid as suitable acid $(H^+)_m Z^{m-}$.

The anion $Z^{m-}$ of the protic acid $(H^+)_m Z^{m-}$ can be identical to the anion $Y^{n-}$ of the water-soluble salt $(Cat^+)_n Y^{n-}$.

$(H^+)_m Z^{m-}$ is preferably selected from among HCl, HBr, $HBF_4$, $H_3C—COOH$, HCOOH, $H_3C—O—SO_3H$, $H_3C—SO_3H$, $F_3C—O—SO_3H$, $CH_3—CH_2—COOH$, $H_2SO_3$, $H_2SO_4$, $HNO_3$, $HClO_4$ or $H_3PO_4$.

$(H^+)_m Z^{m-}$ can be added in pure form or preferably in the form of solutions, particularly preferably as aqueous solution. In particular water can also be added separately, e.g. in the form of ice, in order to remove or take up heat at the same time.

$(H^+)_m Z^{m-}$ is preferably added in such amounts that $Cat^+X^-$ is completely converted.

In the addition, both composition and the $(H^+)_m Z^{m-}$ added can be present at elevated temperature. However, a temperature increase is generally not necessary and the addition can be carried out at room temperature.

As a result of addition of $(H^+)_m Z^{m-}$, the anions $X^-$ of the salts $Cat^+X^-$ are converted into the acids HX. The acids HX have only a low solubility in water, as has been indicated above; the acids HX therefore form an organic phase.

The cation $Cat^+$ is then correspondingly present as water-soluble salt $(Cat^+)_m Z^{m-}$. The water-soluble salts $(Cat^+)_n Y^{n-}$, too, can be converted completely or only partly into the water-soluble acids $(H^+)_n Y^{n-}$. An aqueous phase comprising the water-soluble salts $(Cat^+)_m Z^{m-}$ and $(Cat^+)_n Y^{n-}$ or acids $(H^+)_n Y^{n-}$ is therefore obtained.

After addition of $(H^+)_m Z^{m-}$, two phases are therefore formed:

An organic phase which comprises or consists of HX and the abovementioned aqueous phase.

In a preferred embodiment, $(H^+)_m Z^{m-}$ is added in process step b) in such amounts that the pH of the aqueous phase is less than the pKa of HX, in particular at least two units less than the pKa of HX; e.g. at a pKa of octanoic acid of 4.8, the pH of the aqueous solution should then be not more than 2.8. Under such conditions, HX has gone over completely or virtually completely into the organic phase.

Process Steps c) to e)

In process step c), the organic phase is separated off.

The aqueous and organic phases can be separated easily, e.g. by decanting off one phase. An extractant, e.g. an organic solvent, which is miscible with HX can optionally be added. In this way, any residual amount of HX can be extracted from the aqueous phase. The separation is also aided because the volume of the organic phase is increased.

The extractant can also, if desired, be added simultaneously with the acid $(H^+)_m Z^{m-}$ and optionally water in process step b).

As suitable extractants, it is possible to use, for example, hexane, tert-butyl methyl ether, ethyl acetate, alcohols having more than 5 carbon atoms, e.g. heptanol, 2-ethylhexanol, toluene, dichloromethane, trichloroethane, benzene, chlorobenzene, petroleum spirit, pentanone, isoamyl alcohol, dichloroethane, diethyl ether, methyl isobutyl ketone, cyclohexanone, benzyl alcohol, propylene carbonate, ethylene carbonate, dimethyl carbonate or diethyl carbonate.

The aqueous phase obtained is passed over a strongly basic anion exchanger (process step d). A strongly basic anion exchanger binds anions and in return liberates $OH^-$. Thus, the anions $Z^{m-}$ and $Y^{n-}$ are bound and $OH^-$ is liberated.

The aqueous solution obtained therefore now only comprises the hydroxide of the cations $Cat^+$. The protons $H^+$ of the acids react with $OH^-$ to form water.

Customarily strongly basic anion exchangers are adequately known and are commercially available.

When the strongly basic anion exchanger is completely loaded with anions, it has to be regenerated, i.e. the anions taken up are removed again by washing the anion exchanger with an $OH^-$ comprising solution and the anion exchanger is reconverted into the hydroxide form.

In the final process step e), the organic phase (comprising HX) and the aqueous mixture obtained (comprising $Cat^+ OH^-$) is, optionally with addition of further HX, converted into $Cat^+ X^-$ and $H_2O$. In general, the reaction of $Cat^+ OH^-$ with HX to form $Cat^+ X^- + H_2O$ commences immediately at room temperature; a temperature increase is not necessary.

An addition of further HX in process step e) can, in particular, be useful because the cation $Cat^+$ was previously present together with anions $X^-$ and $Y^{n-}$; but since $Y^{n-}$ has been removed, further HX may be required for complete conversion of all $Cat^+$.

When no organic extractant has been used in the previous process steps, only an aqueous phase is obtained. When an extractant has previously been used, an organic phase is naturally also obtained, but this consists essentially only of the extractant. The aqueous phase can easily be separated off again (see above).

HX (from the organic phase and any additional HX) is preferably added in such amounts that the pH of the aqueous phase obtained is greater than the pKa of HX; the pH of the aqueous phase obtained is particularly preferably at least two units greater than the pKa of HX, e.g. at a pKa of octanoic acid of 4.8, the pH of the aqueous phase obtained should then be at least 6.8. Water can, if desired or necessary for further use, be separated off from the aqueous phase by simple methods, e.g. by distillation.

Further Process Steps

Further measures for purifying $Cat^+ X^-$ can optionally be carried out before or after carrying out the process of the invention.

The compositions under a) can, for example, also comprise undesirable cations which have been introduced by a previous use of the ionic liquid $Cat^+ X^-$. These can be, for example, metal cations such as sodium or potassium ions or chemically modified cations $Cat^+$. In the case of imidazolium cations $Cat^+$, addition or substitution reactions can, for example, occur at the carbon atom between the two nitrogen atoms (R2 position in formula I) during various uses. When imidazolium compounds are used as solvent for cellulose, degradation products such as formaldehyde can add on to the R2 carbon atom (R2 in formula I is then a methylol radical).

Such undesirable cations can, for example, be separated off by the molecular distillation of ionic liquids described in WO 2009/027250, preferably after the process described here.

The compositions under a) can, for example, also comprise undesirable acids which have likewise been introduced or formed by a previous use of the ionic liquid $Cat^+ X^-$.

Such acids can, for example, be separated off before carrying out the process described here. The acids can also be, in particular, acids HX which have been formed from the anion $X^-$ by the previous use of the ionic liquid. A method of separating off such acids is described in the patent application EP 11158189.8 (PF 71814). According to this, such acids, in particular HX, can be removed by means of a weakly basic anion exchanger. Weakly basic ion exchangers are those which comprise a polymer having primary, secondary or tertiary amino groups as ion-exchange polymer and can thus bind acids. Here, the acid proton becomes attached to the amino group (quaternization) and the acid anion is bound as counteranion.

Acids HX without being separated off beforehand can be reused in the process of the invention. For this purpose, the HX bound in the weakly basic ion exchanger has to be obtained back. The weakly basic anion exchanger loaded with HX is advantageously firstly rinsed with a base, e.g. NaOH; this firstly forms the corresponding salt of the base, e.g. NaX. The salt (NaX) can easily be converted into HX by addition of an acid and optionally organic solvent. HX, optionally also together with an organic solvent, can then be added as further HX in process step e) (see above).

The process of the invention is a simple and very effective process for purifying salts $Cat^+ X^-$, where $Cat^+ X^-$ are in particular ionic liquids.

Example

Starting Materials

Ionic Liquid ($Cat^+ X^-$):

1-ethyl-3-ethylimidazolium octanoate (EEIM-Oct for short)

As composition, use was made of a composition which had repeatedly been used for dissolving cellulose. This composition comprised EEIM-Oct and as a result of the repeated use comprised water and a series of impurities.

The composition comprised 24.9% by weight of EEIM and 25.8% by weight of Octanoate.

The water content of the composition was 36.7% by weight

The content of further anions $Y^{n-}$ in the composition before and after carrying out the process of the invention is reported in the table.

The content of acid anions as per Table I was determined by capillary electrophoresis before and after carrying out the process of the invention.

In capillary electrophoresis, the various acid anions are separated in an electric field by means of the different migration velocities. For detection, benzoic acid whose UV absorption is at 225 nm is added to the solution.

Procedure

Process Steps a) to c)

4615.4 g of the composition were reacted with 571 g of 95% sulfuric acid, forming EEIM sulfate from EEIM-Oct according to the following reaction equation. An aqueous phase comprising EEIM sulfate and the impurities EEIM-Y and octanoic acid as organic phase are obtained.

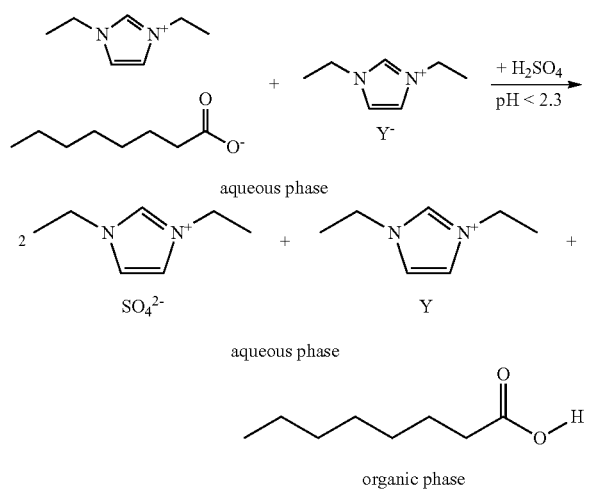

The octanoic acid was then extracted three times with 2.5 l each time of heptane.

Process Step d)

The aqueous phase (4.895 kg) was then passed over a strongly basic ion exchanger (19.2 kg; capacity: 1.15 mol/kg), with the EEIM sulfate and the impurities EEIM-Y being converted into EEIM hydroxide:

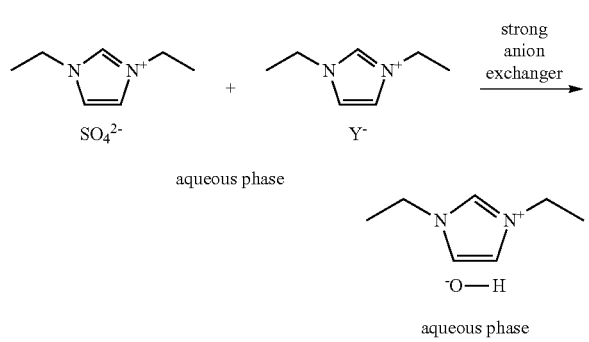

Process Step e)

In the last step, 25 kg of eluate from the ion exchanger (EEIM hydroxide) were reacted with the organic phase from c) (octanoic acid) and with 460 g of fresh octanoic acid to form EEIM-Oct again.

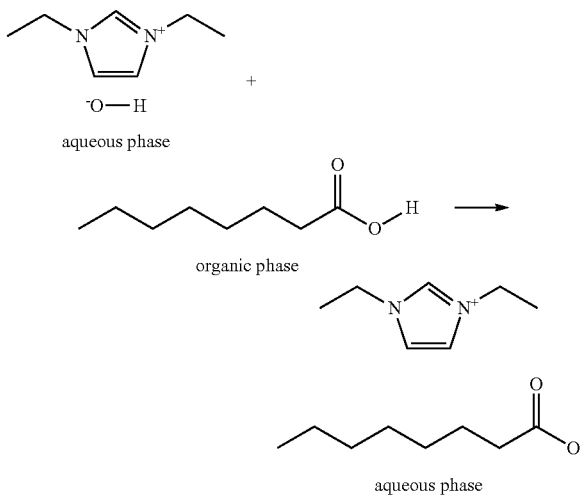

Distillation of the water gave 2.829 kg of EEIM octanoate having a water content of 5%.

TABLE

| | Content of anions $Y^{n-}$: | | | | |
| --- | --- | --- | --- | --- | --- |
| | Before | | After | | |
| Anion | % by weight in solution | Mass ratio of octanoate to anion in % | % by weight in solution | Mass ratio of octanoate to anion in % | After/before Depletion to % of the initial value |
| Octanoate | 24.850 | 100.000 | 47.870 | 100.000 | 100 |
| Formate | 1.110 | 4.467 | 0.140 | 0.292 | 7 |
| Adipate | 0.160 | 0.644 | 0.006 | 0.013 | 2 |
| of glutaric acid | 0.080 | 0.322 | 0.003 | 0.006 | 2 |
| of glycolic acid | 0.110 | 0.443 | 0.040 | 0.084 | 19 |
| Acetate | 0.190 | 0.765 | 0.080 | 0.167 | 22 |
| Lactate | 0.020 | 0.080 | 0.009 | 0.019 | 23 |
| Propionate | 0.080 | 0.322 | 0.040 | 0.084 | 26 |
| of levulinic acid | 0.020 | 0.080 | 0.010 | 0.021 | 26 |
| Chloride | 0.039 | 0.157 | 0.001 | 0.002 | 1 |
| Sulfate | 0.028 | 0.113 | 0.001 | 0.002 | 2 |

The invention claimed is:

1. A process for purifying a salt $Cat^+X^-$, comprising a cation $Cat^+$ and an organic anion $X^-$, the process comprising:
   converting the anion $X^-$ by addition of a water-soluble protic acid $(H^+)_m Z^{m-}$ into an acid HX, thereby forming an organic phase comprising HX and an aqueous phase comprising water-soluble salts $(Cat^+)_m Z^{m-}$ and $(Cat^+)_n Y^{n-}$ or acids $(H^+)_n Y^{n-}$,
   separating off the organic phase,
   passing the aqueous phase over a strongly basic anion exchanger suitable for binding $Z^{m-}$ and $Y^{n-}$ and liberating $OH^-$, thereby obtaining an aqueous mixture comprising $Cat^+OH^-$, and
   converting the organic phase and the aqueous mixture into $Cat^+X^-$ and $H_2O$, optionally with addition of further HX,
   wherein $X^-$ comprises at least 6 carbon atoms,
   prior to the process $Cat^+X^-$ is present as an impurity in a composition comprising a water-soluble salt $(Cat^+)_n Y^{n-}$, Y$^{n-}$ is an inorganic or organic anion different from X$^-$ having not more than 10 carbon atoms,
n is 1, 2 or 3, and
m is 1, 2, or 3.

2. The process of claim 1, wherein the salt Cat$^+$X$^-$ has a melting point of less than 100° C. at 1 bar, atmospheric pressure.

3. The process of claim 1, wherein the salt Cat$^+$X$^-$ is liquid at 21° C., 1 bar.

4. The process of claim 1, wherein Cat$^+$ is an organic cation comprising a heterocyclic ring system and a nitrogen atom as a constituent of the ring system.

5. The process of claim 1, wherein Cat$^+$ is an imidazolium cation of formula I:

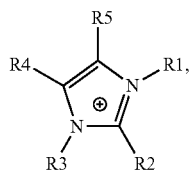

R1 is an organic radical having from 1 to 20 carbon atoms, and
R2, R3, R4, and R5 are each an H atom or an organic radical having from 1 to 20 carbon atoms.

6. The process of claim 1, wherein X$^-$ is an organic anion comprising a carboxylate group.

7. The process of claim 1, wherein X$^-$ is a C6-C20-alkanoate.

8. The process of claim 1, wherein the composition comprises more than 80% by weight of Cat$^+$X$^-$ and optionally a solvent miscible therewith.

9. The process of claim 8, wherein the solvent miscible with Cat$^+$X$^-$ is water.

10. The process of claim 1, wherein the composition comprises from 0.1 to 5 parts by weight of hemicellulose per 100 parts by weight of a total weight of Cat$^+$X$^-$ and solvent.

11. The process of claim 1, wherein Y$^{n-}$ is an organic anion comprising one or two carboxylate groups or at least one inorganic anion selected from the group consisting of chloride and sulfate.

12. The process of claim 1, wherein (H$^+$)$_m$Z$^{m-}$ is at least one selected from the group consisting of HCl, HBr, HBF$_4$, H$_3$C—COOH, HCOOH, H$_3$C—O—SO$_3$H, H$_3$C—SO$_3$H, F$_3$C—O—SO$_3$H, CH$_3$—CH$_2$—COOH, H$_2$SO$_3$, H$_2$SO$_4$, HNO$_3$, HClO$_4$, and H$_3$PO$_4$.

13. The process of claim 1, wherein the separating off the organic phase comprises adding an extractant.

14. The process of claim 13, wherein the extractant is at least one selected from the group consisting of hexane, tert-butyl methyl ether, ethyl acetate, an alcohol having more than 5 carbon atoms, toluene, dichloromethane, trichloroethane, benzene, chlorobenzene, petroleum spirit, pentanone, isoamyl alcohol, dichloroethane, diethyl ether, methyl isobutyl ketone, cyclohexanone, benzyl alcohol, propylene carbonate, ethylene carbonate, dimethyl carbonate, and diethyl carbonate.

15. The process of claim 1, further comprising:
separating off HX with a weakly basic ion exchanger, thereby obtaining a separated HX,
wherein the composition comprises HX as an impurity, and the converting the organic phase comprises adding the separated HX.

16. The process of claim 1, wherein Cat$^+$ is a quaternary ammonium cation.

17. The process of claim 16, wherein the quaternary ammonium cation comprises three or four aliphatic substituents.

18. The process of claim 1, wherein X$^-$ comprises a carboxylate group, a sulfonate group, a sulfate group, or any combination thereof.

19. The process of claim 1, wherein X$^-$ does not comprise any heteroatom that is not an oxygen or sulfur atom in a carboxylate, sulfonate, or sulfate group.

* * * * *